United States Patent
Riederer et al.

(10) Patent No.: US 11,353,530 B2
(45) Date of Patent: Jun. 7, 2022

(54) SYNTHETIC THREE-DIMENSIONAL MAGNETIC RESONANCE IMAGING

(71) Applicant: Mayo Foundation for Medical Education and Research, Rochester, MN (US)

(72) Inventors: Stephen J. Riederer, Rochester, MN (US); Eric A. Borisch, Rochester, MN (US); Roger C. Grimm, Rochester, MN (US); Soudabeh Kargar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 94 days.

(21) Appl. No.: 16/965,146

(22) PCT Filed: Jan. 25, 2019

(86) PCT No.: PCT/US2019/015133
§ 371 (c)(1),
(2) Date: Jul. 27, 2020

(87) PCT Pub. No.: WO2019/147927
PCT Pub. Date: Aug. 1, 2019

(65) Prior Publication Data
US 2021/0041517 A1 Feb. 11, 2021

Related U.S. Application Data

(60) Provisional application No. 62/622,630, filed on Jan. 26, 2018.

(51) Int. Cl.
*G01V 3/00* (2006.01)
*G01R 33/483* (2006.01)
(Continued)

(52) U.S. Cl.
CPC .......... *G01R 33/4835* (2013.01); *A61B 5/055* (2013.01); *A61B 5/7257* (2013.01);
(Continued)

(58) Field of Classification Search
CPC .............. G01R 33/543; G01R 33/5659; G01R 33/3415; G01R 33/36; A61B 5/055
(Continued)

(56) References Cited

U.S. PATENT DOCUMENTS

2017/0061652 A1    3/2017   Chang

FOREIGN PATENT DOCUMENTS

JP         2003233600 A   *   8/2003

OTHER PUBLICATIONS

Barger AV, et al. Time-resolved contrast-enhanced imaging with isotropic resolution and broad coverage using an undersampled 3D projection trajectory Magn Reson Med 2002;48:297-305.
(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

Systems and methods for generating a three-dimensional image of an object from multiple two-dimensional images acquired using a magnetic resonance imaging ("MRI") system are provided. The three-dimensional image has high spatial resolution in all three spatial dimensions. The multiple two-dimensional images can be acquired in one or more orientations (e.g., axial, coronal, sagittal, oblique). The in-plane resolution of these images can be several times finer than the through-plane resolution (i.e., the slice thickness). The images are Fourier transformed along their respective slice orientation direction and processed using the slice profile to generate a Fourier representation of the three-dimensional image with the target spatial resolution. Inverse
(Continued)

Fourier transforming this Fourier representation generates the desired three-dimensional image.

21 Claims, 12 Drawing Sheets

(51) Int. Cl.
  *A61B 5/055*  (2006.01)
  *A61B 5/00*  (2006.01)
  *A61B 6/03*  (2006.01)
  *G01R 33/56*  (2006.01)
  *G01R 33/561*  (2006.01)
  *G06T 5/00*  (2006.01)

(52) U.S. Cl.
  CPC .......... *A61B 6/032* (2013.01); *G01R 33/5608* (2013.01); *G01R 33/5611* (2013.01); *G06T 5/003* (2013.01); *G06T 2207/10081* (2013.01); *G06T 2207/10088* (2013.01); *G06T 2207/20048* (2013.01)

(58) Field of Classification Search
  USPC ......................................................... 324/309
  See application file for complete search history.

(56) References Cited

OTHER PUBLICATIONS

Bernstein MA, et al. "Effect of windowing and zero-filled reconstruction of MRI data on spatial resolution and acquisition strategy." Journal of magnetic resonance imaging: an official journal of the international society for magnetic resonance in medicine 14.3 (2001): 270-280.

Gold GE, et al. Isotropic MRI of the knee with 3D fast spin-echo extended echo-train acquistiion (XETA): initial experience. AJR 2007;188:1287-1293.

Greenspan H, et al. MRI inter-slice reconstruction using super-resolution. Magn Reson Img 2002;20:437-446.

Haider CR, et al. 3D high temporal and spatial resolution contrast-enhanced MR angiography of the whole brain. Magn Reson Med 2008;60:749-760.

Hefnawy, A. A. "An efficient super-resolution approach for obtaining isotropic 3-D imaging using 2-D multi-slice MRI." Egyptian Informatics Journal 14.2 (2013): 117-123.

International Searching Authority. International Search Report and Written Opinion for application PCT/US2019/015133, dated Jul. 3, 2019.

Irani M, et al. Improving resolution by image regisliation. CVGIP: Graphical Models and Image Processing 1991;53:231-239.

Kargar, S., et al. "Use of kZ-space for high through-plane resolution in multislice MRI: application to prostate." Magnetic resonance in medicine 81.6 (2019): 3691-3704.

Kuklisova-Murgasova, M., et al. "Reconstruction of fetal brain MRI with intensity matching and complete outlier removal." Medical image analysis 16.8 (2012): 1550-1564.

Larkman DJ, et al. Use of multiple arrays for separation of signal from multiple slices simultaneously excited. J Magn Reson Img 2001; 13: 313-317.

Mannivannan N, et al. Comparison of super resolution reconstruction acquisition geometries for use in mouse phenotyping. Intl J of Biomedical Imaging 2013;2013:1-11.

Meyer CM, et al. Fast spiral coronary artery imaging. Magn Reson Med 1992;28:202-213.

Mulkern, R. V., et al. "Contrast manipulation and artifact assessment of 2D and 3D RARE sequences." Magnetic Resonance Imaging 8.5 (1990): 557-566.

Riederer, S. et al. "Synthetic 3D Reconstruction" Proceedings of the International Society for Magnetic Resonance in Medicine—Joint Annual Meeting ISMRM-ESMRMB 2018. No 4492. Jun. 1, 2018. Paris, France.

Setsompop K, et al. Blipped-controlled aliasing in parallel imaging for simultaneous multislice echo planar imaging with reduce g-factor penalty. Magn Reson Med 2012;67:1210-1224.

Shilling, R. Z., et al. "A super-resolution framework for 3-D high-resolution and high-contrast imaging using 2-D multislice MRI." IEEE transactions on medical imaging 28.5 (2008): 633-644.

Souza A, et al. Model-based super-resolution for MRI. 30th Annual Intl IEEE EMBS Conf. Vancouver 2008; p. 430-434.

Stevens KJ, et al. Ankle: isotropic MR imaging with 3D-FSE-Cube—initial experience in healthy volunteers. Radiology 2008;249:1026-1033.

Stinson, E. G., et al. "Time-resolved contrast-enhanced MR angiography with single-echo Dixon fat suppression." Magnetic resonance in medicine 80.4 (2018): 1556-1567.

Tamez-Pena JG, et al. MRI isotropic resolution reconstruction from two orthogonal scans. Proc SPIE2001; p. 87-97.

Van Reeth E, et al. Super-resolution in magnetic resonance imaging: a review. Concepts in Magn Reson Part A 2012; 40A: 306-325.

Yan Z, et al. Super resolution of MRI using improved IBP. Intl Conf on Computational Intelligence and Security. 2009; p. 643-647.

* cited by examiner

SYNTHETIC THREE-DIMENSIONAL MAGNETIC RESONANCE IMAGING

CROSS-REFERENCE TO RELATED APPLICATIONS

This application represents the national stage entry of PCT/US2019/015133 filed on Jan. 25, 2019 and claims the benefit of U.S. Provisional Patent Application Ser. No. 62/622,630, filed on Jan. 26, 2018, the contents of which is herein incorporated by reference in its entirety.

STATEMENT REGARDING FEDERALLY SPONSORED RESEARCH

N/A

BACKGROUND

T2-weighted pulse sequences are prevalent in magnetic resonance imaging ("MRI") and are routinely used in the clinical setting. To obtain good quality T2-related contrast generally requires the use of long repetition times and long echo times. As a result, the use of a direct three-dimensional T2-weighted spin echo acquisition is prohibitively long (e.g., several tens of minutes or more), and thus multislice acquisitions are performed instead. Similar issues exist with other MRI pulse sequences and in other medical imaging modalities.

Multiple algorithms have been developed to try to use multiple two-dimensional acquisitions for improved slice resolution, but these algorithms have all been based on mathematical processing in image space.

Thus, there remains an unmet need to allow for the generation of T2-weighted and other magnetic resonance images with high quality spatial resolution in all three spatial dimensions, in particular along the slice-select direction of a multislice acquisition.

SUMMARY OF THE DISCLOSURE

The present disclosure addresses the aforementioned drawbacks by providing a method for generating a three-dimensional image from a set of multiple two-dimensional images acquired with a medical imaging system. A multislice data set comprising a plurality of two-dimensional images acquired with a medical imaging system is provided to a computer system. The two-dimensional images were acquired along a slice orientation direction and each has a slice thickness and is spaced apart by a slice spacing. An intermediate data set is generated by Fourier transforming the multislice data set along the slice orientation direction into k-space. The intermediate data set is converted into Fourier representation data based in part on a slice profile associated with slices depicted in the multislice data set. A three-dimensional image is then generated by inverse Fourier transforming the Fourier representation data along at least the slice orientation direction. The spatial resolution of the three-dimensional image along the slice orientation direction is finer than the slice thickness.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for generating a three-dimensional image of an object from multiple two-dimensional images acquired using a magnetic resonance imaging ("MRI") system. The three-dimensional image has high spatial resolution in all three spatial dimensions. The multiple two-dimensional images can be acquired in one or more orientations (e.g., axial, coronal, sagittal, oblique). The in-plane resolution of these images can be several times finer than the through-plane resolution (i.e., the slice thickness). For example, the two-dimensional images can have an in-plane resolution that is 3-8 times finer than the slice thickness.

The two-dimensional images are Fourier transformed along the slice-select direction. Subsequent processing in k-space is then implemented to improve the spatial resolution along the slice-select direction. As one example, the through-plane resolution can be increased by compensating for the assumed or known profile of each slice. Fourier transformation of these processed k-space data back to image space provides a three-dimensional image set with improved resolution along the original slice select direction.

As noted, the processing of the multislice data sets is done in k-space. It is an aspect of the methods described in the present disclosure that individual slices acquired in a two-dimensional multislice acquisition can be juxtaposed to form a coarsely sampled three-dimensional image. This assemblage of slices can be Fourier transformed along the slice select direction for subsequent processing in k-space. For example, the processing may include correcting for the slice profile used in the RF excitation of the multislice scan. Such processing provides spatial resolution along the slice-select direction that is finer than in the original two-dimensional images.

The input two-dimensional images can, in general, include images acquired along one or more different orientations. For the purposes of illustration, the x-direction can correspond to the anterior-posterior ("A/P") direction, the y-direction can correspond to the left-right ("L/R") direction, and the z-direction can correspond to the superior-inferior ("S/I") direction. In these examples, axial images are those acquired with the slice-select direction along the z-direction.

Figure 1:
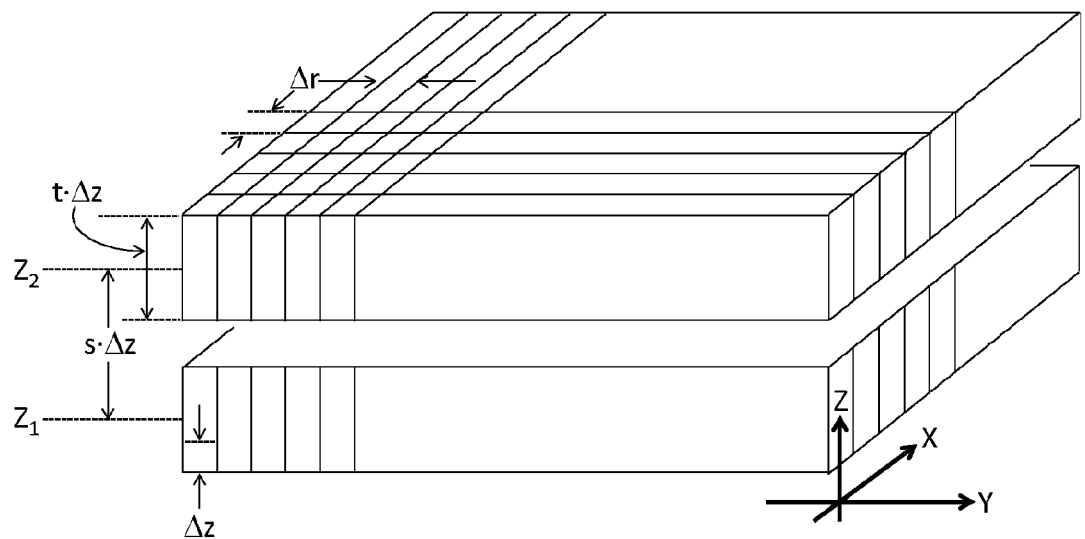
FIG. 1 illustrates an example of two imaging slices obtained in a multislice acquisition.

An example of two axial images is illustrated in FIG. 1. In this example, the lower image is centered at level Z=Z1 and the upper one at Z=Z2. A number of other parameters are also shown. The spatial resolution within the slice, $\Delta r$, is the same along both the x- and y-directions. In practice, the spatial resolution along the x-direction and the y-direction do not need to be equal to each other. In the slice-select direction other parameters are defined. The slice thickness, $t \cdot \Delta z$, and the slice spacing, $s \cdot \Delta z$, are shown. These are both expressed in terms of $\Delta z$, which is the target spatial resolution along the z-direction (i.e., the spatial resolution along the slice-select direction that is desired in the three-dimensional image generated from the two-dimensional images). As one example, $\Delta z$ can be selected as the same size as $\Delta r$.

A typical in-plane resolution, $\Delta r$, can be in the range of 0.4 to 1.0 mm. For single slice or multislice MRI acquisitions, the slice thickness, $t \cdot \Delta z$, can typically be a factor of 3-8 times larger than the in-plane resolution, $\Delta r$, and thus can be larger than the target z-resolution, $\Delta z$, by a similar factor. The slice spacing is the distance along the slice-select direction between the centers of consecutive slices, which in FIG. 1 is listed as $s \cdot \Delta z$.

To be meaningful, both s and t take only positive values. Also, the values of the parameters s and t need not be limited to integer values, but can each have fractional values. The example illustrated in FIG. 1 shows the case in which the slice spacing is larger than the slice thickness (i.e., s>t), thereby causing a gap between consecutive slices. However, it is possible with MRI acquisition for consecutive slices to be spatially contiguous (i.e., s=t) or overlapped (i.e., s<t). In some embodiments of the methods described in the present disclosure, information from overlapping consecutive slices can be used to generate a three-dimensional image with the target resolution, $\Delta z$.

Figure 2A:
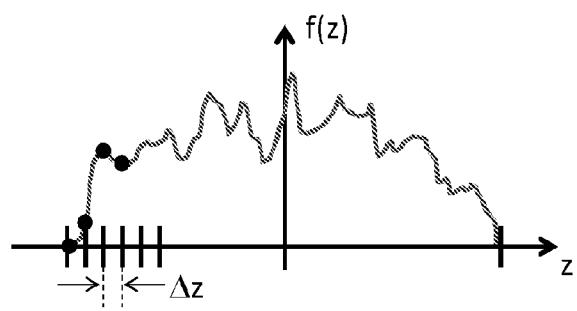
FIG. 2A is an example representation of a target function, such as a target magnetization-of-interest depicted in a magnetic resonance image.

Referring now to FIG. 2A, a reference signal f(z) plotted along the z-direction is shown. In this example, the z-direction corresponds to the slice-select direction. The reference signal, f(z), can correspond to the magnetization-of-interest at each point, z, as determined by the parameters of the pulse sequence, such as the repetition time ("TR") and the echo time ("TE"). When f(z) is presented digitally to a user it can be represented at a resolution of N points at intervals $\Delta z$ across the entire field-of-view ("FOV"). The first few of these discrete samples are shown as black dots in FIG. 2A. As an example, N can be 256 points.

For this discussion, it is assumed that the reference signal, f(z), is unknown. The reference signal can be estimated, however, with the full N-point spatial resolution.

Figure 2B:
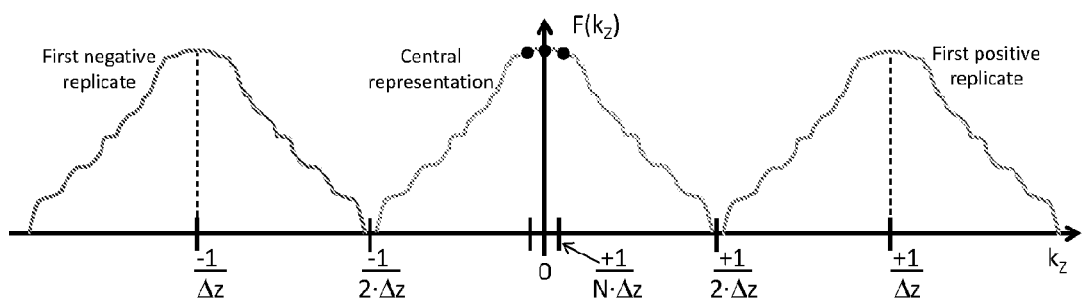
FIG. 2B is an example Fourier spectrum along the slice orientation direction of the target function in FIG. 2A.

The function f(z) has a Fourier transform, F(kZ), which is shown schematically in FIG. 2B. The Fourier transform, F(kZ), can also be computed at discrete samples (e.g., at discrete samples along the $k_Z$-axis). For the typical case of an N-point discrete Fourier transform using the interval $\Delta z$ of the function in FIG. 2A, $F(k_Z)$ is sampled at intervals of $1/(N \cdot \Delta z)$, and the central N samples span the range from $-1/(2 \cdot \Delta z)$ to $+1/(2 \cdot \Delta z)$. Also, the central representation of $F(k_Z)$ is repeated at specific intervals along the $k_Z$-axis in both the positive and negative directions. The spacing between the centerpoints of these replicated versions is equal to $1/\Delta z$, and the replications continue indefinitely in the $+k_Z$ and $-k_Z$ directions. The first replications along each of these directions are shown in FIG. 2B, identified as the "first positive replicate" and "first negative replicate," respectively.

Because of the reciprocity properties of the Fourier transform, if f(z) is known, then $F(k_Z)$ can be determined by direct calculation. Similarly, if $F(k_Z)$ is known or can be estimated, then f(z) can be calculated. As will be described, some embodiments of the techniques described in the present disclosure include determining $F(k_Z)$ from a set of measurements, and then calculating the desired f(z) by inverse Fourier transformation.

In some embodiments of the methods described in the present disclosure, multiple slices are acquired along a single orientation (i.e., slice-select direction). The selection of a slice and the subsequent measurement of the magnetization within that slice effectively integrates the magnetization along the full width of the selected slice. Generally, the slice thickness is larger than the target resolution, $\Delta z$, along the slice-select direction, and thickness values of $3 \cdot \Delta z$ to $8 \cdot \Delta z$ are common.

Ideal slice selection is described as the conversion of longitudinal magnetization to transverse magnetization using a ninety-degree radiofrequency ("RF") pulse, which is effective within the targeted slice, but which creates no transverse magnetization outside of the targeted slice. As one example, for a slice thickness of $4 \cdot \Delta z$, the mathematical function describing the ideal excitation profile would be the following rect function, $$rect\left(\frac{z}{4\cdot\Delta z}\right).$$

Figure 2C:
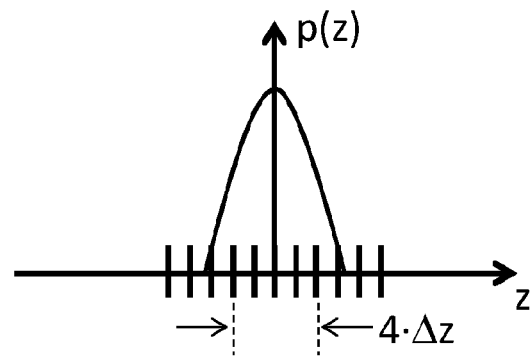
FIG. 2C is an example of a Gaussian-like slice profile.
Figure 2D:
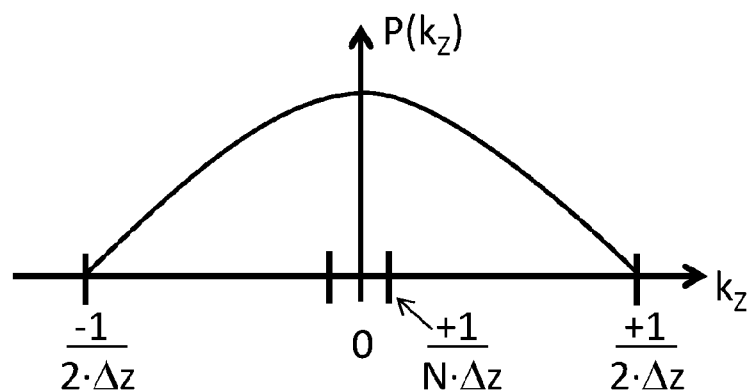
FIG. 2D is a Fourier transform of the Gaussian-like slice profile of FIG. 2C.

In practice, not all magnetization within a slice is ideally excited (e.g., converted from longitudinal to transverse magnetization via a ninety-degree nutation), and some longitudinal magnetization outside of the target slice is converted to non-zero transverse magnetization. To allow for these deviations from the ideal slice profile (e.g., a rect function), the excitation profile can be described as p(z). An example of a Gaussian-like slice profile p(z) that has a width of approximately 4·Δz is shown in FIG. 2C. The slice profile, p(z), has a Fourier transform of its own, which can be described as P(kZ). The Similarity Theorem of Fourier transforms states qualitatively that an increase in the width of a function in one space (e.g., image space) causes a proportionate reduction in the width of the Fourier transform of the function in the conjugate space (e.g., k-space). Thus, as the width of p(z) increases from a narrow impulse centered at z=0 to a width that is several Δz, the width of P(kZ) decreases from a constant, non-zero value for all kZ, to a width of approximately (several Δz)—1. This relationship is reflected in FIG. 2D.

Figure 2E:
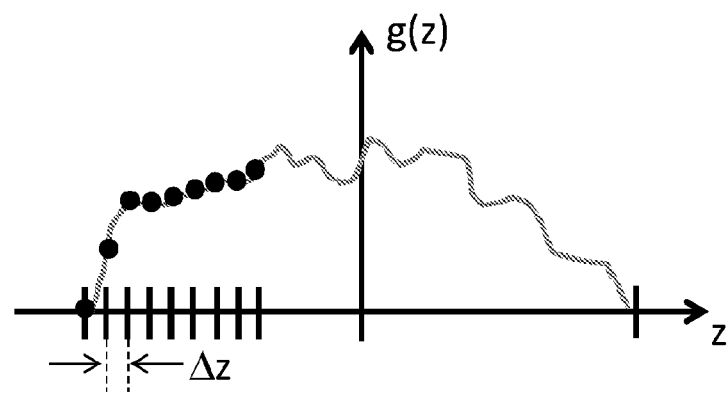
FIG. 2E is a representation of a convolution of the target function of FIG. 2A with the Gaussian-like slice profile of FIG. 2C.

Typically, slice selection is only applied to f(z) at a limited, discrete number of points along the z-direction. However, if each point of the continuous function f(z) were subjected to slice selection, the result could be expressed as the convolution of the function f(z) with p(z). Due to the averaging across the slice profile for each point, z, the result of this convolution would be a blurred version of f(z) along the z-direction. The function resulting from this convolution can be described as the function, g(z), an example of which is illustrated in FIG. 2E.

Figure 2F:
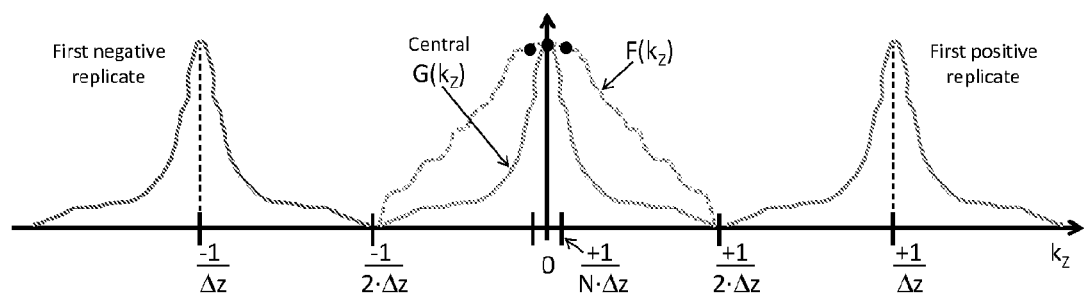
FIG. 2F is a Fourier representation of the convolved function shown in FIG. 2E.

The process of convolving each point of the original f(z) with the assumed slice selection profile p(z) can also be described in k-space. Specifically, the Fourier Convolution Theorem states that the Fourier transform of this convolution is equal to the product of the respective Fourier transforms, namely F(kZ) multiplied by P(kZ) on a point-by-point basis for each $k_Z$. The resulting can be defined as G(kZ), an example of which is shown in FIG. 2F. It is noted that G(kZ) is a narrower version of F(kZ) owing to the falloff of P(kZ) away from the region near $k_Z$=0. This causes a blunting, or attenuation, in the signal power of those $k_Z$ spatial frequencies, which is another manifestation of the effect of averaging across the slice profile. If G(kZ) can be measured, and if P(kZ) were known, then F(kZ) could be recovered using the following formula:

$$F(k_Z) = \frac{G(k_Z)}{P(k_Z)}. \quad (1)$$

For $k_Z$ values for which $P(k_Z)$ is equal to near zero, an undefined value for $F(k_Z)$ can be avoided using various methods, such as adding a small constant to $P(k_Z)$. In that example, the small constant could be selected based on the noise level at $k_Z$.

Figure 2G:
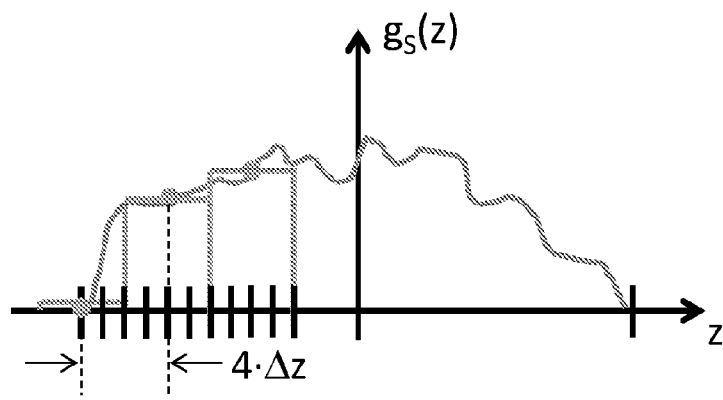
FIG. 2G is the representation of the convolved function in FIG. 2E having overlaid thereon intervals associated with a discrete set of sampled slices.

The example described above assumes that slice selection is done for a continuous range of points, z. However, in practice multislice acquisition is performed with a slice profile p(z) applied to a discrete set of slices, each centered at a corresponding point along the z-direction, as shown in FIG. 2G. For illustrative purposes, in FIG. 2G an interval of 4·Δz has been assumed from one slice to the next, with equal intervals between slices. The first several sampled points are shown in green. Compared to the original assumed 256 points, this acquisition creates 64 samples of g(z) at intervals of 4·Δz. The sampled version of g(z) can be represented as $g_S(z)$, where the subscript "S" denotes the sampled versus continuous version of the function g(z). It is noted that the interval (e.g., 4·Δz in this example) can be selected independently of the slice profile p(z).

Figure 2H:
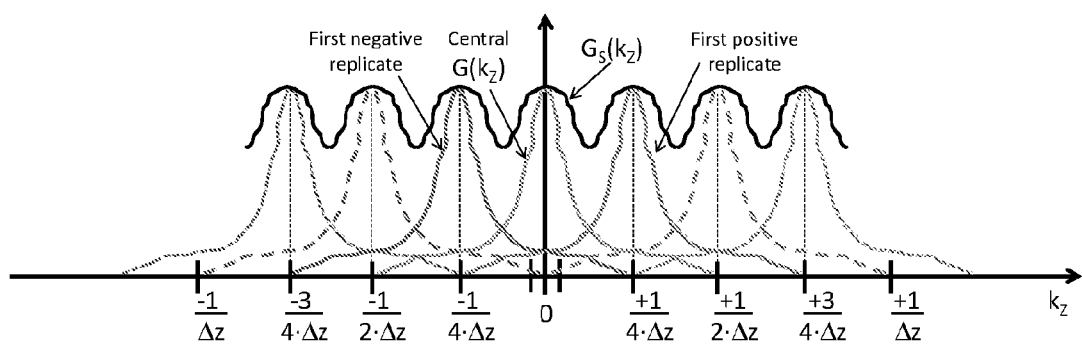
FIG. 2H is a Fourier transform of the discretized convolved function shown in FIG. 2G.

As shown in FIG. 2H, the Fourier transform of $g_S(z)$ can also be calculated, which can be represented as $G_S(k_Z)$. Just as in FIG. 2B, the sampling step in FIG. 2G causes replications of the central function $G(k_Z)$ in k-space along the $k_Z$-axis. However, again invoking the Similarity Theorem, because the spacing between samples has been increased from the 1Δz spacing assumed in FIG. 2A to the 4·Δz spacing assumed in FIG. 2G, the spacing between replications is decreased by this factor, from 1/Δz to 1/(4·Δz). For some regions of negative $k_Z$-space, signals from the first and second (and even third) negative replicates overlap with those of the central primary function. The same happens for some positive $k_Z$ values. The superposition of these replicated signals is what is referred to as aliasing. It is the sum of these signals that is obtained when $G_S(k_Z)$ is calculated. It is noted that except for possible values near $k_Z$=0, the function $G_S(k_Z)$ in general deviates from $G(k_Z)$. Thus, it is not possible to exactly determine $G(k_Z)$ for this specific but common case in which the acquired slices abut. For this reason, investigators have had little reason to Fourier transform acquired data along the slice select direction.

The above has shown how multislice acquisition with the slice select direction along z can be described using analysis along the $k_Z$-direction. In this section it is further described how the multislice acquisition can be adapted to allow accurate estimation of $G(k_Z)$ and hence $F(k_Z)$.

The scenario presented in FIG. 2G and FIG. 2H is a common situation in which the slice spacing is four times the in-plane resolution, and in which the slice thickness nominally matches the slice spacing. As described above, this causes extensive aliasing in the $k_Z$-space representation of this process, which confounds the determination of $G(k_Z)$ and the desired $F(k_Z)$. Consequently, this approach of $k_Z$ analysis is generally not used.

In the methods described in the present disclosure, the replicated versions of $G(k_Z)$ in FIG. 2H can be shifted apart to a greater degree, which can reduce or otherwise eliminate the superposition of the replicates onto the primary $G(k_Z)$ when forming $G_S(k_Z)$, thereby allowing $G(k_Z)$ to be accurately estimated.

The increased shifts along the $k_Z$-direction can be accomplished by decreasing the sampling distance between the slices while maintaining the same slice profile. For slices whose thicknesses nominally match the slice spacing, this will result in the excited slices being overlapped. As one example, then, the desired increased shifts along the $k_Z$-direction can be achieved by using multiple passes of a multislice acquisition with the slice thickness and spacing parameters set as described.

Figure 3A:
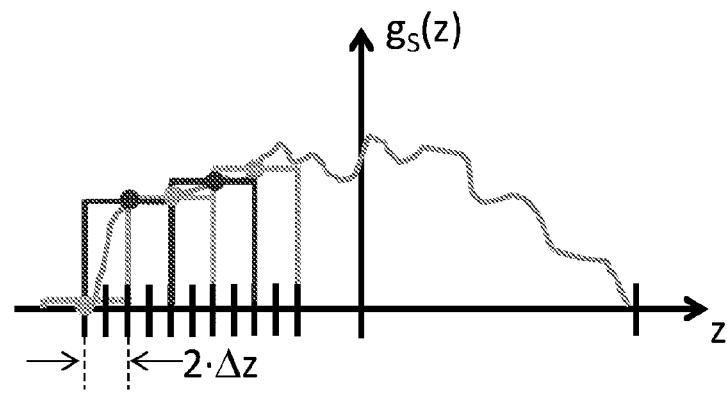
FIG. 3A is a representation of the convolved function of FIG. 2E having overlaid thereon a discretized set of slice profiles with a slice spacing that is half of that represented in FIG. 2G.

This concept is illustrated in FIGS. 3A-3D. FIG. 3A shows the same underlying continuous function g(z) as illustrated in FIG. 2E. That is, the same starting function f(z) and slice profile p(z) have been assumed for this example. However, in this case it is assumed that the increment from one slice position to the next has been set equal to 2·Δz, smaller than the 4·Δz of FIG. 2G. Additional samples at the dark blue points have been interleaved with the previously described green sampled points, and the combination of these is now used. The approximate slice widths are also represented, similar to those in FIG. 2G, but the slices are now overlapped because of the reduced spacing. This sampling can be analyzed in $k_Z$-space similarly to that shown in FIG. 2H, and is presented in FIG. 3B. Because the spacing between slices along the z-direction has been reduced two-fold from $4 \cdot \Delta z$ to $2 \cdot \Delta z$, the spacing between the positions of the replicates of the function $G(k_Z)$ is increased two-fold, from $1/(4 \cdot \Delta z)$ to $1/(2 \cdot \Delta)$. This increased spacing decreases the level of aliasing, causing $G_S(k_Z)$ to more closely match $G(k_Z)$ for many of the $k_Z$ points.

This process of overlapping the slices can be carried further. FIG. 3C shows an example in which the slice spacing is only $1 \cdot \Delta z$. Similar to the reasoning used in describing FIGS. 3A and 3B, this additional two-fold overlap in sampling along the z-direction causes another two-fold increased displacement of the replicated functions along $k_Z$ as shown in FIG. 3D. In this case the replicated functions have no overlap with the central function $G(k_Z)$ over the range from $-1/(2 \cdot \Delta z)$ to $+1/(2 \cdot \Delta z)$. That is to say, $G_S(k_Z)$ formed from the Fourier transform of the discrete samples along the z-direction using the sampling scheme in FIG. 3C, will exactly match $G(k_Z)$ within this range. This in turn allows $F(k_Z)$ to be estimated using Eqn. (1), which allows $f(z)$ to be determined by performing the inverse Fourier transform on $F(k_Z)$.

In some instance, the multiple two-dimensional images to be used as input to the methods described in the present disclosure can be acquired as follows. With multislice acquisitions, once the data have been acquired for one repetition of the acquisition for some slice of interest, recovery of the magnetization within that slice is next allowed to recover before the excitation at the start of the next repetition. During this recovery time MRI measurements can be made for other slices. Depending on the pulse sequence parameters, as many as ten slices or more can be imaged at once with this method. Examples of multislice acquisitions are described below in more detail.

Figure 4:
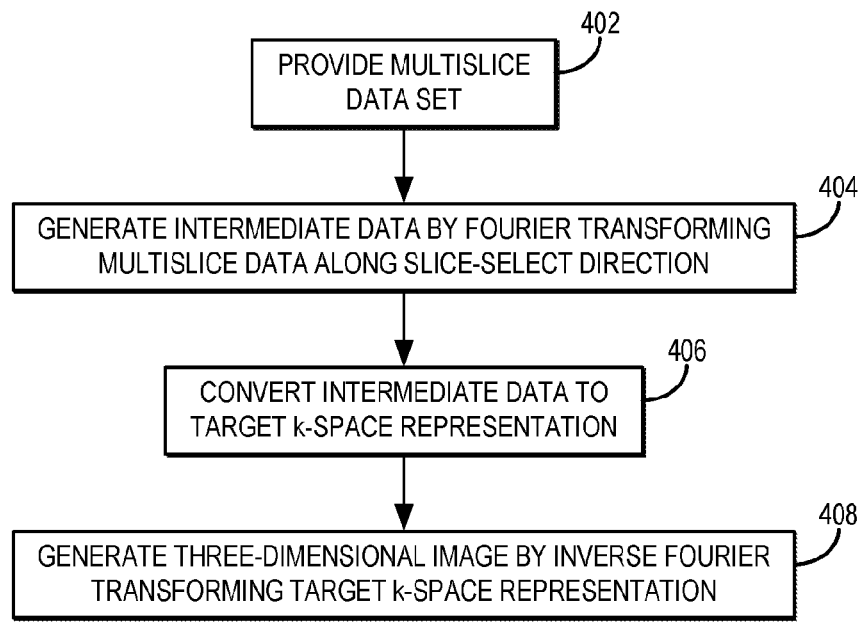
FIG. 4 is a flowchart setting forth the steps of an example method for generating a three-dimensional image with improved spatial resolution along one or more slice orientation directions in accordance with techniques described in the present disclosure.

Referring now to FIG. 4, a flowchart is illustrated as setting forth the steps of an example method for generating a three-dimensional image from multiple two-dimensional images, where the three-dimensional image has a finer spatial resolution along the slice-select direction of the two-dimensional images than the slice thickness of the two-dimensional images.

The method includes providing a multislice data set to a computer system for processing, as indicated at step 402. The multislice data set generally includes a plurality of two-dimensional images acquired for different slices in an imaging volume. In some embodiments, the multislice data set can include two-dimensional images acquired with the same slice orientation (i.e., the images are acquired along the same slice-select direction). In some other embodiments, the multislice data set can include two-dimensional images acquired with two or more different slice orientations (e.g., axial, coronal, sagittal, oblique). In either instance, those slices acquired along a particular orientation form a set of parallel slices.

The multislice data set can be provided by retrieving previously acquired images from a memory or other data storage, or can be provided by acquiring two-dimensional images using an MRI system and providing the acquired images to the computer system, which may form a part of the MRI system.

As noted, the two-dimensional images in the multislice data set can in some instances be acquired with a center-to-center spacing between consecutive Z positions is $s \cdot \Delta z$, where $\Delta z$ is the desired spatial resolution along the z-direction and s is an arbitrary positive number, which may be an integer or non-integer value. The desired spatial resolution, $\Delta z$, is selected to be smaller than the slice thickness so that an improvement in the spatial resolution along the slice-select direction can be achieved.

The images in the multislice data set are then Fourier transformed along their respective slice-select direction to generate intermediate data, as indicated at step 404. For instance, if the two-dimensional images correspond to axial slices that are orientated with the slice select direction along the z-direction, then the Fourier transform is performed along the z-direction to compute the Fourier transform, $G_S(k_Z)$. In this example, the images are not Fourier transformed along the x-direction or the y-direction and thus information in these directions remains in image space. In some embodiments, however, the images may also be Fourier transformed along the other spatial dimensions (e.g., the x-direction, the y-direction, or both, in the example where the z-direction is the slice-select direction). There can be advantages to each approach. Processing in image space can be simpler because it can use reconstructed magnitude values. Processing in k-space can preserve phase dependence, which might be important in some applications.

The intermediate data are converted to a function, $F(k_Z)$, as indicated at step 406. As an example, the intermediate data can be converted as follows. In $k_Z$-space, it can be assumed that some unknown central function of interest, $F(k_Z)$, that is centered at $k_Z=0$ with allowed non-zero values on an interval such as the interval $-1/(2 \cdot \Delta z)$ to $+1/(2 \cdot \Delta z)$ exists. Replicates of this function are created, where the replicates are centered at positions $k_Z=\pm n/(s \cdot \Delta z)$ for integer values of n. Next, the values of the function, $F(k_Z)$, can be defined over the interval (e.g., over $-1/(2 \cdot \Delta z)$ to $+1/(2 \cdot \Delta z)$) as follows. For regions of $k_Z$ which the central $F(k_Z)$ does not overlap significantly with any of its replicates, the function $F(k_Z)$ can be estimated as, $$F(k_Z) = \frac{G_S(k_Z)}{P(k_Z)}; \qquad (2)$$

where $P(k_Z)$ is the Fourier transform of the desired slice profile, $p(z)$. For regions in which there is overlap, an algorithm can be used to define $F(k_Z)$ in some manner, including the possibility of defining $F(k_Z)=0$. Alternatively, $F(k_Z)$ could be continuously extended from small $k_Z$ values where there is limited or no overlap. Also, allowance for $k_Z$ points for which $P(k_Z)$ is equal to or near zero can be accommodated as described above.

The inverse Fourier transform of the function, $F(k_Z)$, is then computed to generate a three-dimensional image with finer spatial resolution along the slice-select direction of the multislice data set, as indicated at step 408. In some instances, assumed values for $F(k_Z)$ of zero or otherwise for $k_Z$ values within and outside of the range (e.g., $-1/(2 \cdot \Delta z)$ to $+1/(2 \cdot \Delta z)$) can be used.

As noted above, the two-dimensional images in the multislice data set are acquired using a slice profile, $p(z)$. In some instances, the slice profile can be a rect function, which is used to describe perfect excitation (i.e., complete conversion of longitudinal to transverse magnetization) within the slice and creation of no transverse magnetization outside the slice. In some instances, it may be advantageous to acquire images with a slice profile that is different from the ideal rect function.

A slice profile can be generally selected on the basis that its Fourier transform $P(k_Z)$ be known or well-defined. If $P(k_Z)=0$ at any $k_Z$, then the correction of Eqn. (1) is not defined mathematically and other corrections may need to be implemented. As one example, corrections can be implemented using regularization, in which a small positive value is added to $P(k_Z)$ for all $k_Z$ values.

By selecting or otherwise designing a slice profile, p(z), to cause $P(k_Z)$ to have a more benign behavior in $k_Z$-space, such as having positive values for all $k_Z$ values of importance, an otherwise arbitrary slice profile can be implemented. For example, if p(z) is devised to be a Gaussian function with a nominal width matching the desired slice thickness, then its Fourier transform $P(k_Z)$ is also Gaussian. Gaussian functions are non-negative at all points, and thus there would be no points with $P(k_Z)=0$.

Thus, the methods described in the present disclosure can implement arbitrary slice profiles, including those that might have traditionally undesirable features, such as a gradual falloff of response versus the slice-select direction (e.g., the z-direction). In fact, processing in $k_Z$-space readily allows for arbitrary slice profiles. Slight deviations from an exact rect function can be accommodated within p(z) and its Fourier Transform, $P(k_Z)$.

The above description in Eqn. (2) for the correction (e.g., unblurring) of the slice profile $P(k_Z)$ can be performed using alternative mathematical approaches. It will be appreciated by those skilled in the art, for instance, that division by a function $P(k_Z)$ in one space (in this case $k_Z$-space) is equivalent to deconvolution of the Fourier transform of $P(k_Z)$ in the conjugate space (in this case Z-space). Yet, additional mathematical approaches can be formulated using statistical estimation of the desired function $F(k_Z)$ based on the entirety of the measured data set, $G(k_Z)$.

In some instances, the multislice data set can be converted to a new slice profile, q(z), having Fourier transform, $Q(k_Z)$. This can be accomplished by first forming the intermediate k-space function as described above. This intermediate function would then be multiplied by $Q(k_Z)$ on a point-by-point basis in $k_Z$-space to form $F(k_Z)$. An inverse Fourier transform would then be applied to $F(k_Z)$ to form the desired three-dimensional image, f(z).

In some embodiments, the multislice data set can be acquired using acceleration techniques, including intra-slice acceleration techniques. Acceleration techniques are commonly performed in MRI to speed up the acquisition. For 2D multislice acquisitions, acceleration techniques can include a variety of methods that can be performed along the frequency encoding (e.g., readout) direction, or along the phase encoding direction. Examples of such in-plane acceleration techniques include partial Fourier sampling, which may also be referred to as fractional echo if performed along the readout direction; fast-spin-echo in which multiple phase encodes are sampled per TR interval; and parallel acquisition, such as with SENSE or GRAPPA, both of which allow undersampling along the phase encode direction.

Because these accelerated acquisition techniques are applied to an individual slice for which a position along the slice-select direction is fixed, which results in a standard two-dimensional image for that position (e.g., a Z position along the z-direction), subsequent use of that reconstructed slice for processing along Z or $k_Z$ (for axial images) as described in the present disclosure can still be implemented. That is to say, the methods described in the present disclosure are compatible with intra-slice, or in-plane, acceleration.

Acceleration in the slice-select direction can also be implemented, such as through the use of simultaneous multislice ("SMS") acquisitions. In SMS techniques, multiple slices along a given slice-select direction (e.g., the z-direction for axial images) are excited with a single RF pulse (e.g., a multiband RF pulse). The resulting magnetic resonance signals are encoded within the $k_X$–$k_Y$ plane (for a slice-select direction oriented along the z-direction) and individually reconstructed. SMS techniques allow for multiple slices (e.g., 2-3) to be sampled by a single excitation, which effectively enables more slices to be imaged within a given time. Similar to the intra-slice acceleration methods described above, these through-plane accelerations can be used to more rapidly acquire a multislice data set that can be processed using the methods described in the present disclosure. SMS techniques do not otherwise provide improved resolution along the slice-select direction by accounting for the slice profile, but SMS techniques can be combined with the methods described in the present disclosure to provide such an improvement.

Figure 3B:
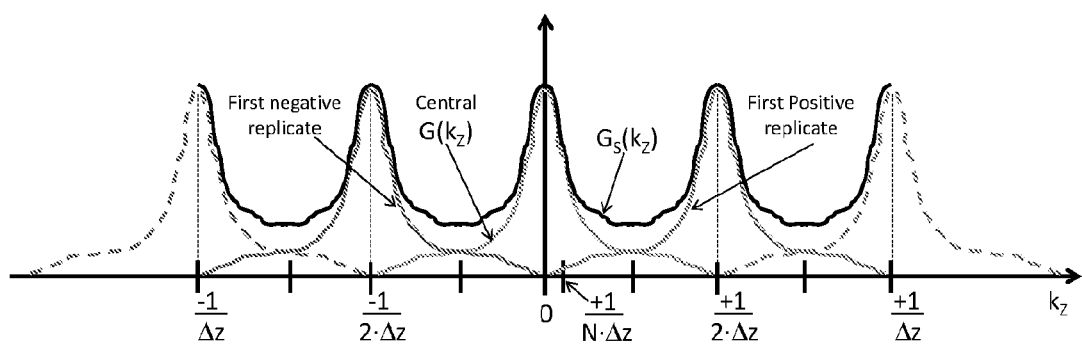
FIG. 3B is a Fourier transform of the discretized function shown in FIG. 3A.
Figure 3C:
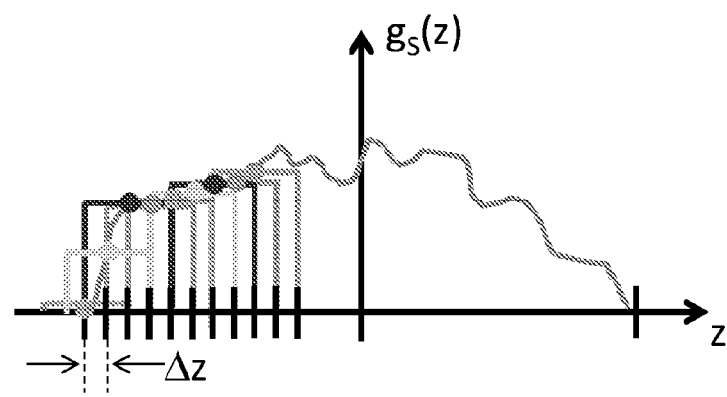
FIG. 3C is a representation of the convolved function of FIG. 2E having overlaid thereon a discretized set of slice profiles with a slice spacing that is one-quarter of that represented in FIG. 2G.
Figure 3D:
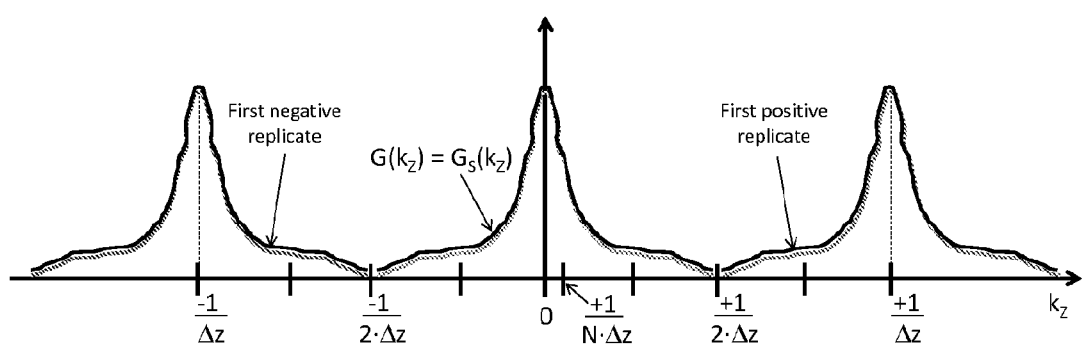
FIG. 3D is a Fourier transform of the discretized function shown in FIG. 3C.

In describing FIGS. 2H, 3B, and 3D, it was noted that the degree of superposition of the aliases of $F(k_Z)$ is dictated by the sampling interval, s·Δz, used when acquiring the data in the multislice acquisition. As the sampling interval is made closer to Δz (i.e., the targeted spatial resolution along the slice-select direction, which may be the z-direction) these superpositions are reduced. However, making the sampling interval progressively smaller from, say, 4·Δz to 1·Δz will require proportionately longer scan time to acquire the more densely sampled data if the same overall coverage along the slice-select direction is desired.

Because the signal power in k-space of a two-dimensional image formed with a multislice acquisition is heavily concentrated near the k-space origin and becomes considerably smaller in magnitude further from the origin, a relatively small sampling interval (e.g., 1·Δz) can be used when sampling k-space near the k-space origin, and larger sampling intervals (e.g., 2·Δz or 3·Δz) can be used when sampling k-space at higher spatial frequencies. With such an approach, less acquisition time is needed than if the same sampling interval of 1·Δz were used for all k-space values. Because of the diminished signal power at the higher spatial frequencies (i.e., larger k-space values), the effect of the aliasing at such values due to the larger sampling interval will be reduced.

Thus, in some embodiments, the multislice data set can be acquired with differential sampling along the slice-select direction, as described above, to balance between scan time and aliasing.

The methods described in the present disclosure are applicable to any acquisition in which a set of parallel images is collected, or in which multiple sets of such images are collected along different slice orientations, generally with the through-plane resolution being coarser than the in-plane resolution. Multislice acquisitions are commonly performed for T2-weighted spin-echo imaging ("T2SE"), which typically requires TR values of 2000 ms or longer. However, other types of pulse sequences can be implemented to acquire magnetic resonance images with different types of image contrast. One example is diffusion-weighted imaging ("DWI") in which TR values exceeding 3000 ms are common, and in which multislice acquisitions are used. Yet another example is 2D FLAIR imaging, which uses inversion recovery in the magnetization evolution phase with overall TR times exceeding 6000 ms.

Although the methods described in the present disclosure have been presented as methods for improving the spatial resolution in magnetic resonance images, the techniques can also be adapted for other medical imaging modalities in which one or more sets of parallel images are acquired. As one particular example, x-ray computed tomography ("CT") commonly acquires images of parallel sections of an object, and with contemporary scanners the consecutive sections are often overlapped. This acquisition scheme results in sampling in the direction orthogonal to the plane of the slices that is finer than the slice thickness, matching what was described in FIGS. 2A-2H. If images are acquired in this manner, the original CT images can each be assigned a slice position, Fourier transformed along that slice direction, and subjected to processing similar to that described previously. The slice profile of the CT scan can either be measured or modeled, providing the functions p(z) and P($k_Z$). Although modern CT detectors have very fine intrinsic resolution along the principal axis of the table, such detectors can have gaps between the detector elements in that direction, causing lost efficiency in dose utilization. The methods described in the present disclosure can effectively eliminate the dead space from these gaps in the detector.

The methods described above were generally described for those instances where images are acquired with only one slice orientation (e.g., axial as used in the examples above). As noted above, the methods described in the present disclosure can also be applied to multislice acquisitions in which images are acquired with two different slice orientations. This might be the case when two orientations are desired by the clinician. The embodiments described below can provide high resolution images in the remaining orientation, and in some instances improved resolution images in the original orientations.

For the purpose of illustration, the following examples are described with respect to acquiring a multislice data set having a set of axial images and a set of sagittal imaged. In such an example, the slice-select direction for the axial images is the z-direction and the slice-select direction for the sagittal images is the y-direction. The target spatial resolution in all three spatial direction is $\Delta r$.

In the single orientation scenario described with respect to FIGS. 2A and 2B, $f(z)$ was the desired function of interest, and it had Fourier transform F($k_Z$). In the dual orientation case, $f(x, y, z)$ can be the unknown function of interest with Fourier transform F($k_X$, $k_Y$, $k_Z$). This Fourier transform, F($k_X$, $k_Y$, $k_Z$), can be modeled or estimated from the acquired multislice data, from which the target $f(x, y, z)$ can be calculated by inverse Fourier transform.

Figure 5:
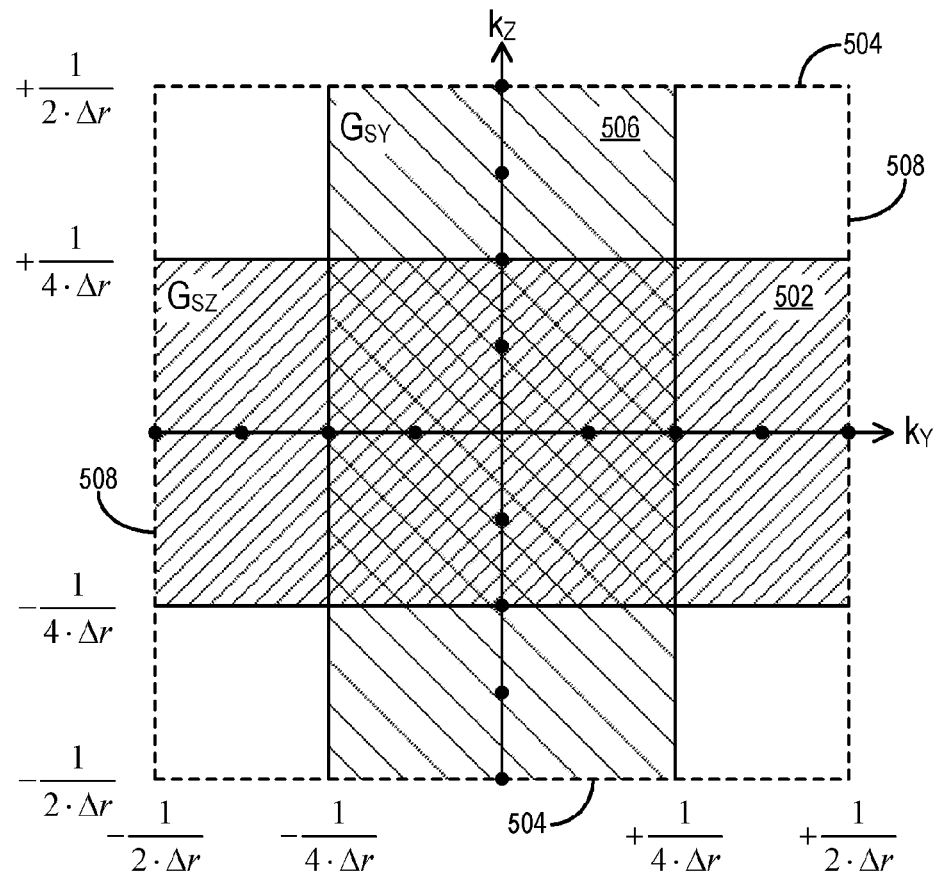
FIG. 5 is a representation of $(k_Y, k_Z)$ space into which a set of axial images were Fourier transformed along the z-direction and a set of sagittal images were Fourier transformed along the y-direction.

As an example, the axial images have slice thickness $t \cdot \Delta r$ and slice spacing $s \cdot \Delta r$. The k-space data $M_{SZ}(k_X, k_Y, Z_i)$ are collected and assigned to their corresponding positions, $Z_i$, along the z-axis. Here the first subscript "S" denotes the sampled version of $f(x, y, z)$ in conjunction with slice selection, analogous to the single orientation case. The second subscript "Z" indicates the direction of slice selection. Fourier transformation along the z-direction yields the result $G_{SZ}(k_X, k_Y, k_Z)$ which can be described in three-dimensional k-space as shown in FIG. 5. In FIG. 5, sampling along the slice-select direction, $k_Z$, and the phase-encode direction, $k_Y$, are illustrated. The third direction, $k_X$, is not shown, but can be assumed to be sampled during the readout of both the axial and sagittal acquisitions at the target spatial resolution, $\Delta r$.

Analogous to the discussion pertaining to FIGS. 2E and 2F above, for an assumed slice thickness of $t \cdot \Delta r$ the central representation of the signal power of the measured data covers a width of approximately $2/(t \cdot \Delta r)$ along the $k_Z$ direction. For the specific case of a slice width of $4 \cdot \Delta r$ (i.e., t=4), this central region of $G_{SZ}(k_X, k_Y, k_Z)$ is depicted in the horizontal band 502 identified as "$G_{SZ}$" in FIG. 5. Also, due to the slice spacing of $s \cdot \Delta r$, the central representation is replicated at intervals of $\pm n/(s \cdot \Delta r)$ along the $k_Z$ slice-select direction. For the specific case of a spacing of $2 \cdot \Delta r$ (i.e., s=2), the first replicates along the $\pm k_Z$ directions would be centered at $k_Z = \pm 1/(2 \cdot \Delta r)$. These positions are shown by the horizontal dashed lines 504 in FIG. 5.

The general goal of magnetic resonance image acquisition and processing is to sample the magnetic resonance signal in k-space from the origin outward to some desired target. For the one-dimensional case in FIG. 2B, this was from $k_Z = 0$ out along the $k_Z$ axis to $k_Z = \pm 1/(2 \cdot \Delta z)$, where $\Delta z$ was the target spatial resolution. For the dual-orientation case, this is from the ($k_Y, k_Z$) origin (in this particular example) outward to the desired targets in both the $k_Y$ and $k_Z$ directions. For the assumed case here in which the target resolution is $\Delta r$ for both the y-direction and the z-direction, this might extend outward to encompass a square in FIG. 5 with the corners at the four points ($k_Y$, $k_Z$)=($\pm 1/(2 \cdot \Delta r)$, $\pm 1/(2 \cdot \Delta r)$). However, sampling out to these points is not required for adequate quality images, and the extent of coverage can potentially be relaxed. For example, good image quality can be obtained with sampling out to some circle with radius $k_R = 1/(2 \cdot \Delta r)$, where $k_R = \sqrt{k_Y^2 + k_Z^2}$. This might be even further relaxed while retaining high quality.

For purposes of discussion, the above description assumed that the target resolution $\Delta r$ was the same in the y-direction and the z-direction. In some embodiments, however, the target resolution in each slice-select direction can be different (e.g., $\Delta y \neq \Delta z$), in which case the same goal of k-space coverage would apply but the square and circular regions would become rectangular and elliptical in shape.

For the set of images formed from the sagittal multislice acquisition, the slice-select direction is the y-direction, as mentioned above. As one example, the slice thickness can be $t \cdot \Delta r$ and the slice spacing can be $s \cdot \Delta r$; however, slice thicknesses and slice spacing different from those used for the first image set can also be used. The acquired data can be represented as $M_{SY}(k_X, Y_i, k_Z)$ and assigned to their respective slice positions along the y-direction. Fourier transform along the y-direction thus yields $G_{SY}(k_X, k_Y, k_Z)$. This result can be assigned in ($k_Y, k_Z$) with corresponding central region and axes of replicates, but now along the $k_Y$-direction. This is shown in FIG. 5 with the vertical band 506 identified as "$G_{SY}$" again assuming t=4 and s=2. The center positions of the first replications are shown as vertical dashed lines 508.

Formation of the target F($k_X$, $k_Y$, $k_Z$) can be performed in various ways. For regions in which one of the sampling functions, $G_{SZ}$ or $G_{SY}$, is well known, but the other is not, then F($k_X$, $k_Y$, $k_Z$) can be determined from the well-known function by some transformation. For example, if slice selection is performed for the axial orientation with a slice profile, p(z), that has a Fourier transform, P($k_Z$), then the following relationship can be used:

$$F(k_X, k_Y, k_Z) = \frac{G_{SZ}(k_X, k_Y, k_Z)}{P(k_Z)}. \quad (3)$$

Just as for the single orientation case, some care may be needed for $k_Z$ values for which P($k_Z$) is equal to or near zero. This might apply, for example, to the leftmost blue shaded region of FIG. 5, where $G_{SZ}$ is well known between $k_Y = 1/(2 \cdot \Delta r)$ to $-1/(4 \cdot \Delta r)$, and between $k_Z = 1/(4 \cdot \Delta r)$ to $+1/(4 \cdot \Delta r)$.

For regions in which both of the sampling functions are well known, then both can be used to estimate the target. For example, the process in Eqn. (3) could be done for the axial and sagittal orientations and the two results averaged. Finally, for regions in which neither sampling function is well known, $F(k_X, k_Y, k_Z)$ can be estimated from some combination of the two sampling functions, such as based on the level of aliasing of each, or alternatively a value of zero could be assigned.

As in the single orientation implementation described above, the target high spatial resolution image, $f(x, y, z)$ is generated as the inverse Fourier transformation of $F(k_X, k_Y, k_Z)$.

The above description assumed that the directions of slice encoding for the two multislice scans were orthogonal to each other. In some instances, the two slice orientations do not need to be exactly orthogonal. In these instances, the two rectangular shaped sampling regions of FIG. 5 would be slightly skewed from each other, and the sampled points of the two scans would not be positioned on the same rectilinear grid. The methods described in the present disclosure can still be used in these instances. As one example, the two sampling functions could be used separately to form an estimate for $F(k_X, k_Y, k_Z)$, and the estimates could be added with some proper accounting for skewness during the combination step. As another example, the samples from the two scans could be placed onto a common grid in $(k_Y, k_Z)$ space. For instance, interpolation could be used to convert the samples to a common grid. Estimation of $F(k_X, k_Y, k_Z)$ would then proceed as described above.

Additionally or alternatively, the systems and methods described in the present disclosure can be implemented to improve the through-plane resolution in multislice MRI based in part on modifying the data acquisition such that the order in which data are acquired within individual passes of a multislice acquisition is altered so as to eliminate or substantially reduce scalloping artifacts and other such artifacts. For instance, the data acquisition can be interleaved amongst multiple passes within a multislice acquisition to cause the acquisition times for the different passes to overlap. As a result, periodic scalloping behavior in the reconstructed images can be reduced.

There is interest in improving the through-plane resolution of multislice acquisitions. One approach is to attempt to deal with the above technical issues of direct thin-slice acquisition. Another approach is to use slices with conventional slice thicknesses (e.g., 3 mm or thicker), but to acquire them in such a way that the slices are overlapped. Using superposition or spatial filtering along the slice select direction can potentially provide through-plane spatial resolution finer than the slice thickness itself. Related to these, another approach is the technique of simultaneous multislice in which multiple slices are excited and interrogated within the same repetition interval. This does not improve through-plane resolution directly, but allows for an increased number of slices to be imaged per unit time.

Figures 6A, 6B:
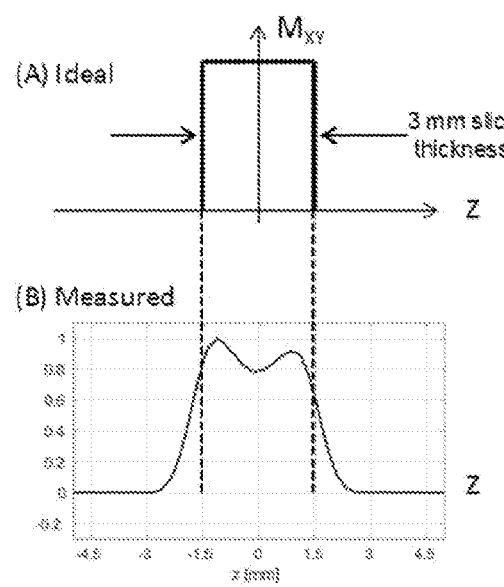
FIGS. 6A-6B show examples of an ideal slice profile (FIG. 6A) and a measured slice profile (FIG. 6B).

These approaches all make use of "selective excitation" of each slice of interest. A characteristic of selective excitation is that the actual magnetization that is excited by the selective RF pulse does not, in general, exactly match a perfect slice. This is illustrated in FIGS. 6A-6B, which plot the excited magnetization (i.e., transverse magnetization $M_{XY}$ tipped away from longitudinal magnetization $M_Z$) as a function of distance along the slice select direction (e.g., the Z direction).

As an example, excitation of a slice having 3.0 mm thickness centered at position Z=0 ideally creates a slice profile that has unit value for ±1.5 mm centered about Z=0, and which is zero valued outside this range. That is, the slice profile is perfectly "rectangular" as shown in FIG. 6A. In practice, however, multiple phenomena such as finite RF pulse width cause the actual slice profile to not have instantaneously changing values at the edges of the slice. A measured profile with nominal 3.0 mm thickness is shown in FIG. 6B. Note that this has non-zero $M_{XY}$ outside the dashed lines defining the 3.0 mm slice. A consequence of this is that if the desired slices are close together along the Z direction, the excitation of one slice may undesirably cause small but nonetheless objectionable excitation of a nearby slice. It is common in multislice acquisitions for the nominal slice thickness to match the slice-to-slice incremental spacing. This can be referred to as "abutting" slices. In the example shown in FIGS. 6A-6B, note that due to the effects of the slice profile illustrated in FIG. 6B that excitation of a slice can cause artifactual partial excitation of its abutting neighbors.

As the name implies, multislice acquisitions typically involve the acquisition of many slices within a scan. The above-described problem associated with slice-to-slice interference can be generally avoided as follows. Suppose that N abutting slices are to be acquired, with N=20. Then, in practice, Slices 1, 3, 5, . . . , 19 are imaged in one multislice acquisition or "pass," and Slices 2, 4, 6, . . . , 20 are imaged in a second pass. Images reconstructed from the two passes are then combined and presented in the proper order as Slices 1, 2, 3, . . . , 19, 20.

With multislice acquisitions, the slice thickness and the slice spacing are separate parameters. For a given slice thickness it is possible to choose slices that abut, choose slices that have a gap between them, or even to acquire slices that are overlapped. The latter is of interest when it is desirable to generate an image set that can have finer resolution along the slice select direction than that imposed by the slice profile, such as by using the methods described above. With overlapped slices the issue of interference of excitation of one slice on its nearest neighbor slices becomes more serious than for abutting slices. Here too, this is generally addressed by acquiring all desired slices using multiple passes of the acquisition.

Figure 7:
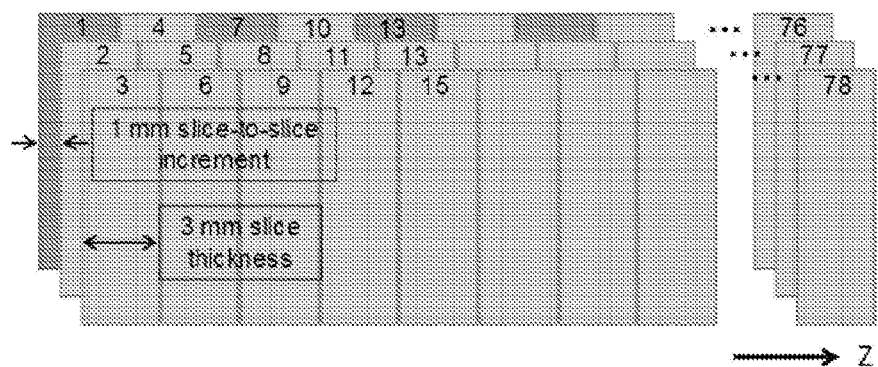
FIG. 7 is an example of a conventional overlapped multislice acquisition.

An example of the acquisition of overlapped slices is shown in FIG. 7. In this case suppose that a total of 78 slices are to be acquired, each with 3 mm slice thickness and with a 1 mm slice-to-slice increment, where the slice-to-slice increment refers to the distance between centers of consecutive slices. Depending upon the specific slice profile of the acquisition, there are multiple ways in which passes can be defined to avoid slice interference. As one example, assume that the excitation of Slice 7 does not affect the magnetization in Slices 1 and 13 shown (i.e., the spatial extent of the slice selection does not go beyond a full slice thickness in the +Z and −Z directions). In this case, all of these slices and the further multiples (19, 25, . . . , 73) can be identified as those belonging to Pass 1. Similarly, other groups of slices can be identified and imaged within additional passes. For example, Pass 2 can include Slices 2, 8, 14, . . . , 74; Pass 3 can include Slices 3, 9, 15; and so on. In the example shown in FIG. 7, a total of six passes are used to acquire all 78 slices.

Figure 8:
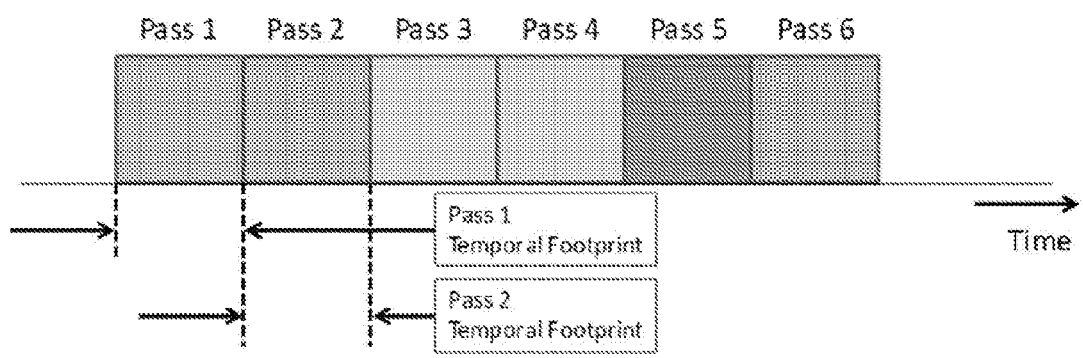
FIG. 8 illustrates multiple different passes in a multislice acquisition each having the same temporal footprint.

The overall time for acquiring these slices is depicted in FIG. 8. This shows schematically the consecutive acquisition of six passes of data, each pass including multiple slices (e.g., 13 slices, as in this example). The "temporal footprint" can be defined as the time over which any data are acquired which are used to form the slices within an individual pass.

For the above description, all data are acquired for the slices within Pass 1 before the acquisition moves on to Pass 2, and the temporal footprints of both passes are shown. Although the durations are the same, there is no overlap in time between the temporal footprints for Passes 1 and 2. The same holds for the remaining passes in the acquisition; the six footprints all have the same duration but there is no temporal overlap between any of them.

Figures 9A, 9B, 9C:
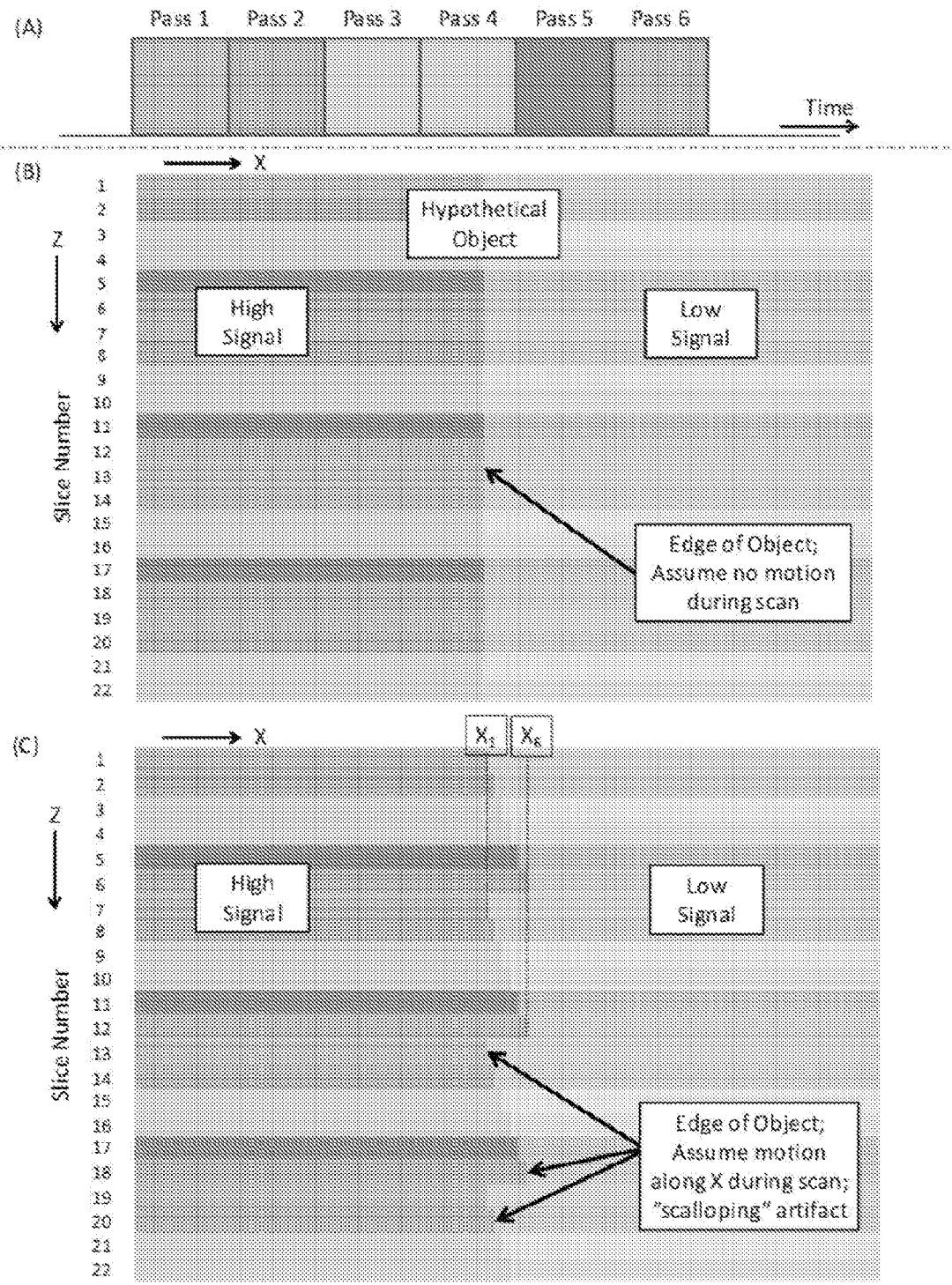
FIGS. 9A-9C illustrate the effect of motion in creating a scalloping artifact when using a conventional multislice acquisition.

The association of elapsed time over the course of the scan and the slice sampling of the object being imaged is portrayed in FIGS. 9A-9C. In this example suppose that the slices sample the object consecutively from top to bottom along the presumed Z slice select direction, with Slice 1 at the top. Assuming the same apportionment of slices into six passes as described in FIGS. 7 and 8, Slices 1, 7, 13, etc. are shown as being sampled within Pass 1, all pictured in blue in FIGS. 9A-9B. Similarly, Slices 2, 8, 14, etc. are within Pass 2, and so forth for all six passes. For this example, in FIG. 9A assume that there is no variation of signal in the object along the Z direction. However, along the X direction, presumed to be left/right (L/R) in the figure, suppose that there is an edge within the object under study, created by relatively high signal to the left of the edge and low signal to the right. This might be caused, for example, by a lesion with relatively high signal next to normal tissue with relatively low signal, the signal difference created by the TR and TE of the pulse sequence.

In FIG. 9A it was presumed that there is no motion over the course of the scan. In this case the edge is portrayed as being at the same X position from top to bottom of the image. However, suppose next that there is slight left-to-right motion which occurs over the course of the scan. For ease of description in this example, suppose that the object is at a specific position for the entirety of the measurement of Pass 1, is shifted slightly to the right for the entirety of Pass 2, shifted by the same amount further to the right for Pass 3, and this continues for all six passes of the acquisition. Because Slices 1, 7, 13, etc. are all measured with Pass 1, they all portray the edge at the same X position. This is shown as X1 in FIG. 9C. Similarly, because Slices 2, 8, 14, etc. are all measured within Pass 2, they portray the edge at a different location along X. This continues for all six passes of the acquisition, with the edge for the slices in Pass 6 at location X6. This results in the portrayal of the edge in Slices 1-6 as progressing from left to right. However, in going from Slice 6 to 7, because Slice 7 was created from data acquired within Pass 1 of the scan at the time of the initial location of the edge, there is an abrupt jump backward, in the negative X direction. This occurs not only for Slices 6 to 7, but for every transition from a slice acquired in the final pass of the scan to a slice created from the first pass, in this example from Slices 12 to 13, 18 to 19, etc. The result of this is a periodicity in the behavior of the edge location from top to bottom of the image. This is undesirable, artifactual behavior. Because there are typically multiple such periods along the Z extent of the image, this can be referred to as "scalloping."

In the above discussion it was assumed that the object was changing during the course of the scan because of motion along the X direction. Motion in any direction transverse to the slice select direction can cause this effect. Also, scalloping can occur due to effects other than motion. For example, if the magnetization level within the group of slices changes over the course of the entire scan, such as due to incoming flow of fully magnetized spins, then differential changes from one pass to the next can cause the slices formed from different passes to have different signal levels.

Similar to the above argument for periodic motion of the position of the signal edge, this will result in periodic or scalloping-like behavior of the signal level.

Understanding the methods described in the present disclosure is benefitted by a review of how data are acquired for slices contained in an individual pass with conventional methods. As above, for purposes of illustration suppose that six passes are required to sample all desired slices and that the slices comprising Pass 1 are Slices 1, 7, 13, etc. where consecutive numbers correspond to consecutive positions along the slice select axis, here assumed to be Z.

As is known to those skilled in the art, the objective of a two-dimensional (2D) acquisition is to acquire data for all desired $k_X$ and $k_Y$ values for each desired slice along Z. There are multiple ways to acquire this desired data. For illustrative purposes, assume that Cartesian acquisition is performed with the readout direction along X and the phase encode direction along Y, with respective conjugate variables $k_X$ and $k_Y$. Data for a specific slice are progressively accumulated in a series of repetitions of the MRI acquisition, with data for all $k_X$ values acquired for an individual $k_Y$ value within one repetition. If a total of $N_Y$ values of $k_Y$ are desired for image formation, then the number of repetitions of the acquisition $N_{REP}$ is proportional to $N_Y$.

There are several factors which determine this specific proportionality. One of these is any level of averaging of similarly acquired data from multiple repetitions, which might be desired to improve the signal-to-noise ratio ("SNR") of the final image. If this number of averages is $N_{AVG}$, then $N_{REP}$ is also proportional to $N_{AVG}$. A second factor is the concept of fast-spin-echo imaging, in which complete sets of $k_X$ samples are acquired for multiple lines of $k_Y$ within a single repetition. The number of such $k_Y$ lines sampled per repetition is called the echo train length ("ETL"). Fast-spin-echo acquisition provides a proportionate decrease in the number of required repetitions to the ETL. With these considerations the number of repetitions can be represented as:

$$N_{REP} = \frac{(N_{AVG} \times N_Y)}{ETL}. \tag{4}$$

The number repetitions can be further reduced if acceleration methods (e.g., SENSE or GRAPPA) are used. For an acceleration factor $R_Y$ along the phase encode direction, Eqn. (4) is modified as:

$$N_{REP} = \frac{(N_{AVG} \times N_Y)}{(ETL \times R_Y)}. \tag{5}$$

As one non-limiting example, values for these parameters can be $N_{AVG}=2$, $N_Y=320$, $ETL=20$, and $R_Y=2$, leading to $N_{REP}=16$.

The above describes how the number of repetitions is determined for data acquisition for an individual slice. The repetition time ("TR") used for MRI data acquisition is determined by the desired contrast in the image. For T1-weighted images TR is typically in the range of 300 to 500 msec. For T2-weighted imaging TR is generally no smaller than 2000 msec. In both of these cases the TR is generally much longer than the time required to sample the number of echoes (i.e., the ETL) within the echo train. After the echoes are measured within one repetition, the magnetization within that slice must recover back toward equilibrium before the next sampling of that slice is done in the next repetition.

As described above, some conventional implementations of multislice acquisitions include sampling second, third, and even more slices during the recovery time between successive excitations of the first slice. These concepts are shown pictorially in FIG. 10, which depicts the sampling of the slices within Pass 1 of the acquisition described earlier. These are Slices 1, 7, 13, . . . , 73, a total of 13 slices. This number, 13, is chosen to fill up the repetition interval with as many slices as possible. The acquisition starts with the data for Repetition 1 being measured for Slices 1, 7, 13, etc. Then, after Slice 73 is measured for Repetition 1, Slice 1 is measured for Repetition 2, followed by Slices 7, 13, etc., as before. This process continues for all requisite repetitions of the acquisition, $N_{REP}$, so as to acquire all required data for all slices comprising Pass 1.

With current practices, the above process for Pass 1 is repeated for all passes in the acquisition as may be necessary to image all desired slices. In this example, this is six passes. As described earlier, this lack of any temporal overlap in the passes leads to the scalloping artifact along the Z direction.

It is a discovery of the methods described in the present disclosure that the scalloping artifacts can be reduced or otherwise removed by subdividing the repetitions within a pass and acquiring the subdivided data over the entirety of the scan time.

Figure 10:
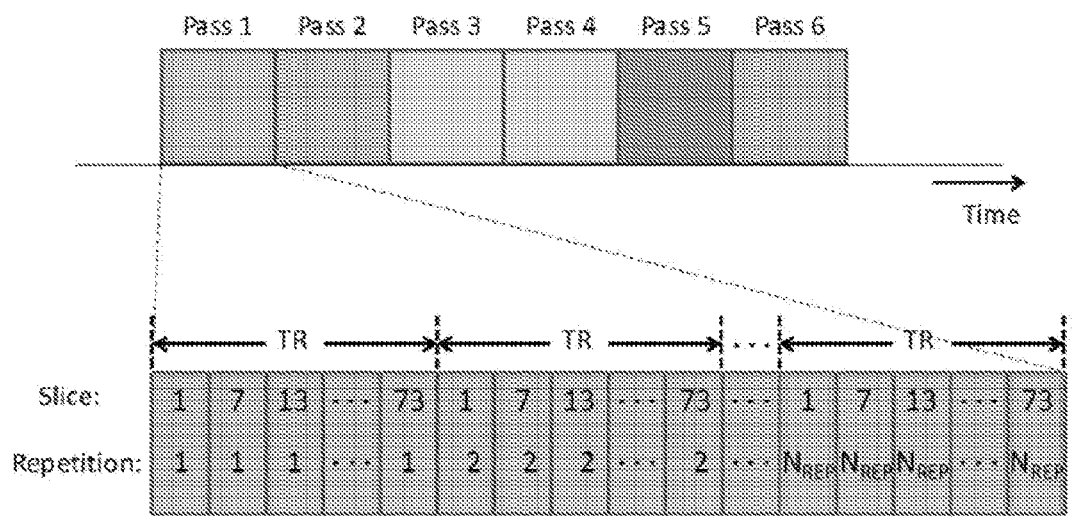
FIG. 10 shows an example of a pass in a multislice acquisition that contains a subset of repeated slices.

As described in FIG. 10, the acquisition of data for a pass requires $N_{REP}$ repetitions. Defining a segment as some subset of these repetitions, multiple segments of the repetitions can be formed such that the combination of all segments represents all $N_{REP}$ repetitions. It is understood that an individual repetition of the acquisition for a pass corresponds to the sampling of all slices that are included within that pass. It is convenient, but not necessary, that all segments be equal in size. For example, if $N_{REP}=16$ as in the above example, a segment could be defined as containing four repetitions, with Segment 1 defined as data collection for Repetitions 1-4, Segment 2 as collection for Repetitions 5-8, etc.

Figures 11A, 11B, 11C, 11D:
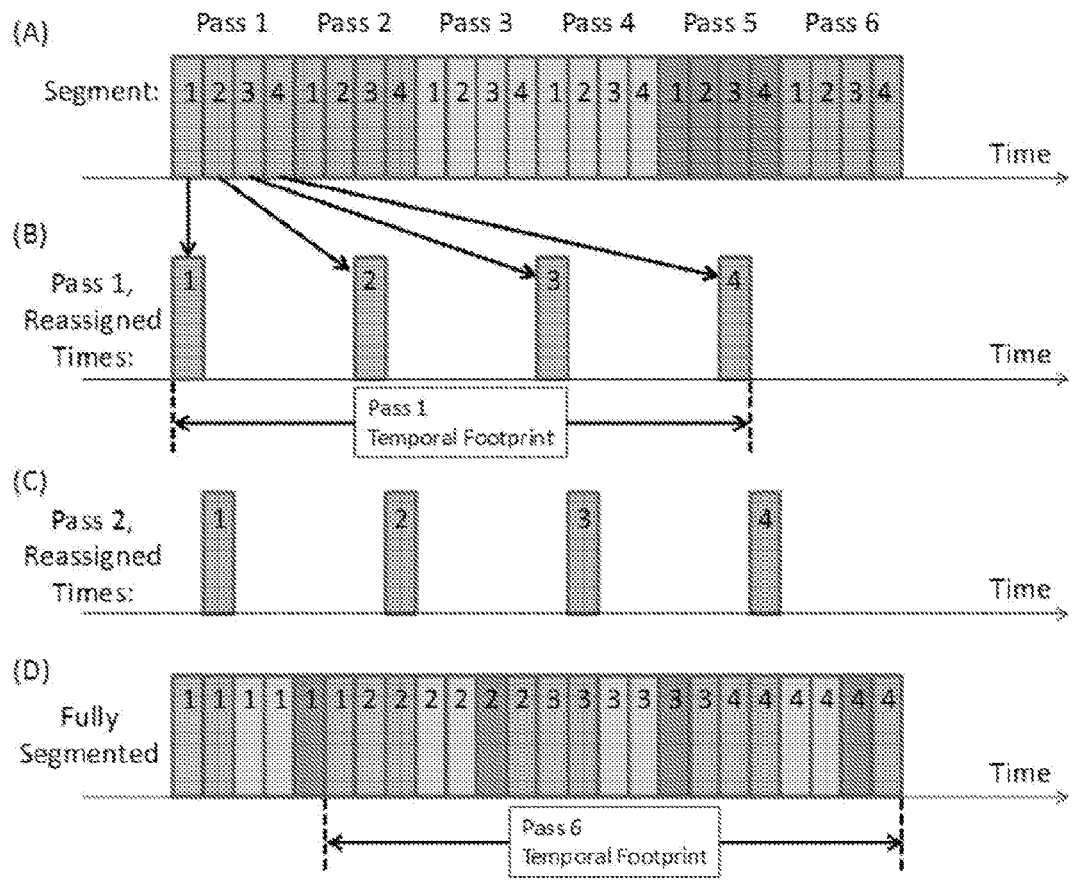
FIGS. 11A-11D illustrate an example of a multislice acquisition with segmented passes, as described in the present disclosure.
Figures 12A, 12B:
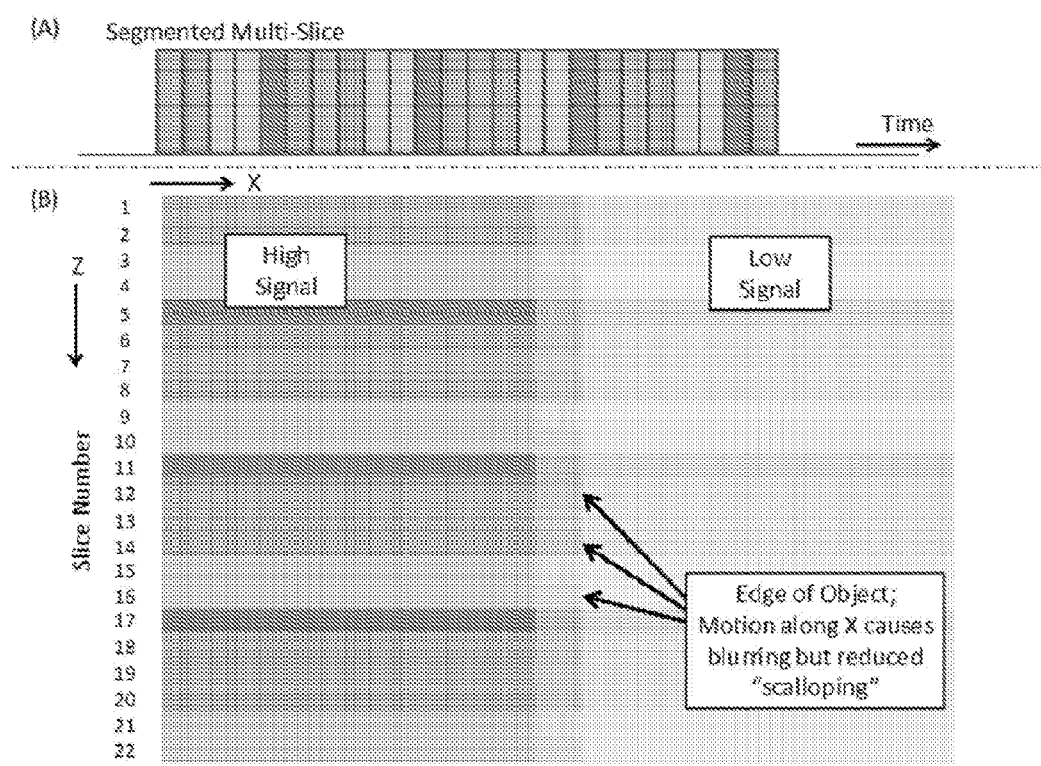
FIGS. 12A-12B illustrate how a segmented-pass multislice acquisition reduces scalloping artifacts.

With the methods described in the present disclosure, various segments corresponding to an individual pass are acquired across substantially the complete acquisition duration. This is shown schematically in FIGS. 11A-11D. Suppose that Pass 1 is apportioned into four segments. With the conventional acquisition these would be acquired one after the other as shown in FIG. 11A. However, these can alternatively be reassigned to be sampled across the entire scan as shown in FIG. 11B. With this reapportionment the temporal range over which these are sampled, defined previously as the temporal footprint, is now extended.

The same procedure above can be applied to the other passes of the acquisition. FIG. 11C shows this for Pass 2, which is similarly subdivided into four segments. These are likewise assigned to times across the overall acquisition. The result of performing this process of segmentation and time reapportionment for all six passes is shown in FIG. 11D. Here, each pass is shown in a separate color; each pass is sampled with four segments, all numbered in the figure; all segments from all passes are assigned acquisition times across the overall acquisition. FIG. 11D also shows the temporal footprints for Passes 1 and 6, the footprint for Pass 1 starting earliest in the overall scan and that for Pass 6 ending at the end of the scan. As seen, there is considerable overlap in time between these two footprints, and it can be readily shown that the temporal footprints for the other passes, Passes 2-5, also have considerable temporal overlap.

It is possible to look at the impact of this altered acquisition in the presence of presumed left-to-right motion along the X direction similar to that considered earlier for FIG. 9B. The data for Pass 1 is now acquired starting at the very start of the scan and is completed near the end. Thus, those slices included within this pass are now all subject to motion occurring over essentially the entire scan. This will result in a blur at the edge between the high and low signal areas of the object for these slices (Slices 1, 7, 13, etc.). This is shown in FIGS. 13A-13B. Next consider the slices for Pass 2 (Slices 2, 8, 14, etc.). Data acquisition for these slices similarly extends from near the start to near the end of the scan, and thus any motion-related unsharpness occurs over substantially the same time as for Pass 1, resulting in similar blur for these slices. This same logic holds for all six passes comprising the scan. The final result is that the edge between high to low signal in the reconstructed object is now blurred, but importantly is not subject to the prominent and distracting scalloping artifact from before.

In some instances, one or more repetitions of the RF pulses and gradients contained in a pulse sequence are performed, but without collecting data for the final image. The purpose of these "dummy repetitions" is to convert the magnetization from its initial state, typically at full magnetization along the direction of the principal magnetic field, into a state which is near the steady state reached during the playout of the repetitions used for data collection. This steady state is typically some fraction of the full magnetization. Failure to account for this can potentially result in artifacts in the final images due to different or inconsistent magnetization levels across the measurements.

As described above, the individual passes included in a scan of abutting or overlapped slices are actually separate scans. One or more dummy repetitions are performed at the start of each. In some instances, it may be advantageous to use dummy repetitions for each segment in the segmented-pass multislice acquisitions described in the present disclosure. Including these dummy repetitions can provide consistent signal level across all segments in a pass. These dummy repetitions can be readily incorporated in the methods described above. Whether dummy repetitions are needed (or otherwise useful), and the number of such dummy repetitions, can be determined experimentally and will likely depend on factors such as the number of passes of the scan, the number of segments to be used, and the repetition time.

Figure 13:
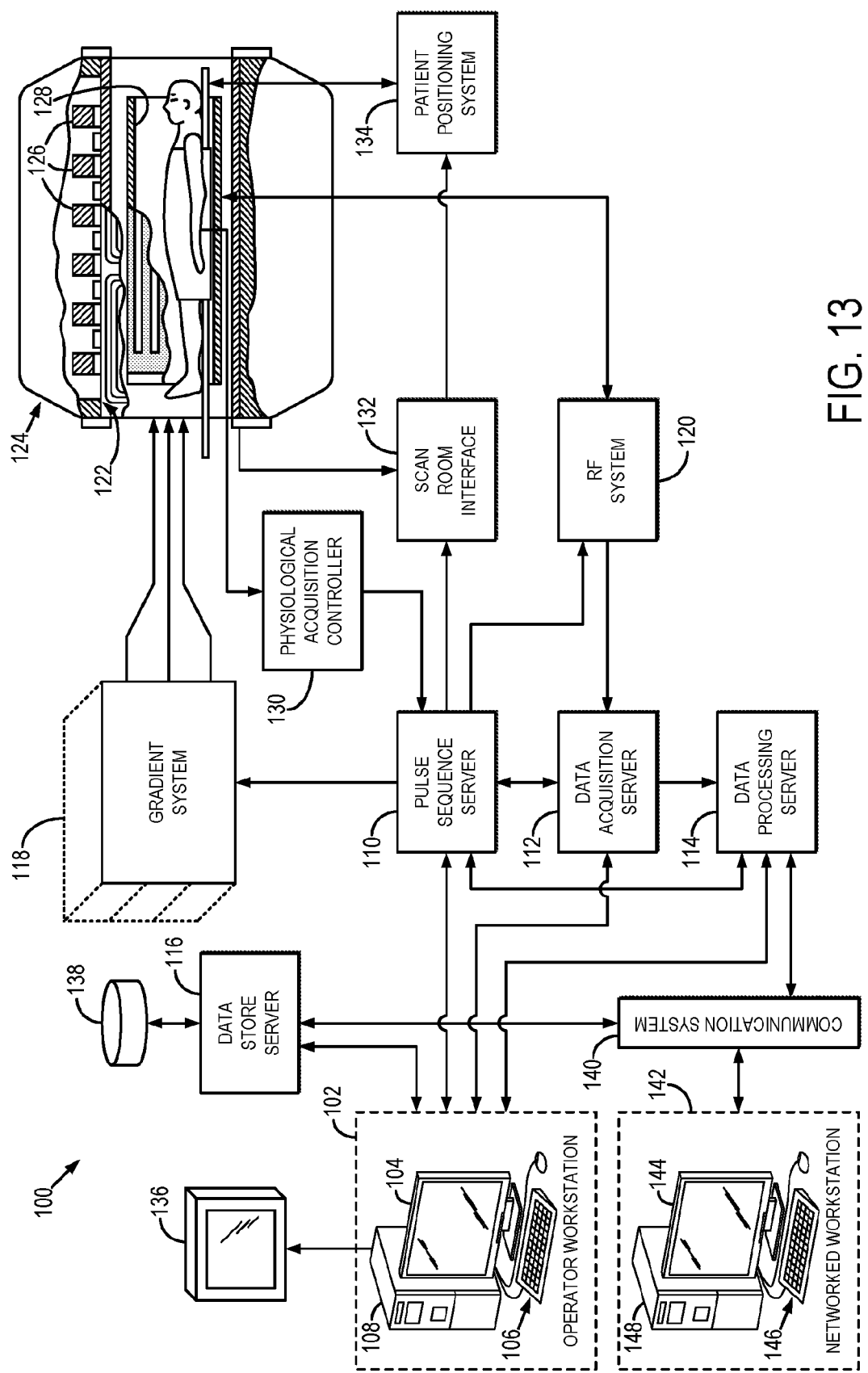
FIG. 13 is a block diagram of an example MRI system that can implement the methods described in the present disclosure.

Referring particularly now to FIG. 13, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (6);$$

and the phase of the received magnetic resonance signal may also be determined according to the following relationship:

$$\varphi = \tan^{-1}\left(\frac{Q}{I}\right). \qquad (7)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a three-dimensional image from a set of multiple two-dimensional images acquired with a medical imaging system, the steps of the method comprising:
    (a) providing to a computer system, a multislice data set comprising a plurality of two-dimensional images acquired with a medical imaging system, wherein the two-dimensional images were acquired along a slice orientation direction and each have a slice thickness and are spaced apart by a slice spacing;
    (b) generating an intermediate data set with the computer system by Fourier transforming the multislice data set along the slice orientation direction into k-space;
    (c) converting the intermediate data set into Fourier representation data with the computer system, based in part on a slice profile associated with slices depicted in the multislice data set; and
    (d) generating a three-dimensional image with the computer system by inverse Fourier transforming the Fourier representation data along at least the slice orientation direction, wherein the spatial resolution of the three-dimensional image along the slice orientation direction is finer than the slice thickness.

2. The method as recited in claim 1, wherein step (c) includes converting the intermediate data into the Fourier representation data by dividing the intermediate data by a Fourier transform of the slice profile.

3. The method as recited in claim 1, wherein at least one of the slice thickness or slice spacing is selected to minimize superposition of k-space replicates in the Fourier representation data.

4. The method as recited in claim 3, wherein the slice thickness and the slice spacing are selected such that each of the plurality of two-dimensional images partially overlaps with adjacent ones of the plurality of two-dimensional images.

5. The method as recited in claim 3, wherein the slice spacing is selected as a positive valued multiple of the spatial resolution of the three-dimensional image along the slice orientation direction.

6. The method as recited in claim 5, wherein the positive valued multiple is a positive integer multiple.

7. The method as recited in claim 6, wherein the slice spacing is selected from a range of $1 \cdot \Delta r$ to $4 \cdot \Delta r$, wherein $\Delta r$ is the spatial resolution of the three-dimensional image along the slice orientation direction.

8. The method as recited in claim 1, wherein the slice profile is one of a rect function or a Gaussian function.

9. The method as recited in claim 1, wherein:
    the multislice data set comprises a first plurality of two-dimensional images acquired with the medical imaging system along a first slice orientation direction and each having a first slice thickness and being spaced apart by a first slice spacing, and a second plurality of two-dimensional images acquired with the medical imaging system along a second slice orientation direction that is different from the first slice orientation direction and each having a second slice thickness and being spaced apart by a second slice spacing;
    step (b) includes generating the intermediate data set by Fourier transforming the first plurality of two-dimensional images along the first slice orientation direction into k-space and the second plurality of two-dimensional images along the second slice orientation direction into k-space; and
    wherein the three-dimensional image has a first spatial resolution along the first slice orientation direction that is finer than the first slice thickness and a second spatial resolution along the second slice orientation direction that is finer than the second slice thickness.

10. The method as recited in claim 9, wherein the first slice thickness and the second slice thickness are a same slice thickness.

11. The method as recited in claim 9, wherein the first slice spacing and the second slice spacing are a same slice spacing.

12. The method as recited in claim 9, wherein the first plurality of two-dimensional images has a first slice profile and the second plurality of two-dimensional images has a second slice profile, and wherein step (c) includes converting the intermediate data based in part on both the first slice profile and the second slice profile.

13. The method as recited in claim 1, wherein step (c) includes converting the intermediate data to the Fourier representation data by multiplying the intermediate data point-by-point with a Fourier transform of a different slice profile than the slice profile associated with the multislice data set.

14. The method as recited in claim 1, wherein the multislice data set is acquired using a magnetic resonance imaging (MRI) system.

15. The method as recited in claim 14, wherein the multislice data set is acquired using at least one of an in-plane acceleration technique or a simultaneous multislice acquisition technique.

16. The method as recited in claim 14, wherein the multislice data set is acquired using an acquisition technique wherein k-space data acquired within a specified distance from an origin of k-space are acquired with a first sampling density along the slice orientation direction and k-space data acquired beyond the specified distance from the origin of k-space are acquired with a second sampling density along the slice orientation direction that is different from the first sampling density.

17. The method as recited in claim 1, wherein the multislice data set is acquired with an x-ray computed tomography (CT) system.

18. The method as recited in claim 1, wherein the multislice data set is acquired with a magnetic resonance imaging (MRI) system using a pulse sequence in which:
    slices corresponding to the plurality of two-dimensional images are assigned into a plurality of passes such that the excitation of any of the slices assigned to a given pass does not significantly affect magnetization of any other slice assigned to the given pass;
    repetitions for sampling each slice are subdivided into a discrete number of segments, wherein the discrete number of segments ranges from one to a total number of the repetitions;
    segments for each of the plurality of passes are assigned across an acquisition time; and
    data are acquired for all slices and for all of the plurality of passes is performed using the assignment of segments across the acquisition time.

19. The method as recited in claim 18, wherein the segments for each of the plurality of passes are assigned across the acquisition time such that gaps of time exist between each consecutive segment in each pass.

20. The method as recited in claim 19, wherein segments from different passes are interleaved in the gaps of time.

21. The method as recited in claim 18, wherein one or more dummy repetitions are performed at a start of each segment.

\* \* \* \* \*